(12) United States Patent
Luu et al.

(10) Patent No.: US 7,169,400 B2
(45) Date of Patent: Jan. 30, 2007

(54) WATERLESS LOTION AND LOTION-TREATED SUBSTRATE

(75) Inventors: Phuong Van Luu, Appleton, WI (US); David W. White, Clintonville, WI (US); Jacob H. Propp, Oshkosh, WI (US); Brian J. Schuh, Appleton, WI (US)

(73) Assignee: Fort James Corporation, Atlanta, GA (US)

( * ) Notice: Subject to any disclaimer, the term of this patent is extended or adjusted under 35 U.S.C. 154(b) by 557 days.

(21) Appl. No.: 10/141,442

(22) Filed: May 7, 2002

(65) Prior Publication Data

US 2003/0211124 A1 Nov. 13, 2003

(51) Int. Cl.
*A61K 8/02* (2006.01)
*A61K 8/06* (2006.01)

(52) U.S. Cl. ............... 424/400; 424/401; 424/402; 514/937

(58) Field of Classification Search ........ 424/400, 424/401, 402; 514/937; 252/816; 162/158, 162/179
See application file for complete search history.

(56) References Cited

U.S. PATENT DOCUMENTS

| 4,767,625 A | 8/1988 | Mitsuno et al. |
|---|---|---|
| 5,240,562 A | 8/1993 | Phan et al. |
| 5,427,696 A | 6/1995 | Phan et al. |
| 5,525,345 A * | 6/1996 | Warner et al. ............... 424/402 |
| 5,607,760 A | 3/1997 | Roe |
| 5,624,676 A | 4/1997 | Mackey et al. |
| 5,665,426 A | 9/1997 | Krzysik et al. |
| 5,705,164 A | 1/1998 | Mackey et al. |
| 5,720,966 A | 2/1998 | Ostendorf |
| 5,830,487 A | 11/1998 | Klofta et al. |
| 5,869,075 A | 2/1999 | Krzysik |
| 5,871,763 A | 2/1999 | Luu et al. |
| 5,980,922 A | 11/1999 | Mackey et al. |
| 5,981,044 A | 11/1999 | Phan et al. |
| 5,994,414 A | 11/1999 | Franco et al. |
| 6,001,381 A | 12/1999 | Gordon et al. |

FOREIGN PATENT DOCUMENTS

| EP | 0875233 A | 11/1998 |
|---|---|---|
| EP | 1050297 A | 11/2000 |
| WO | WO-95/06102 A | 3/1995 |
| WO | WO-97/30216 A | 8/1997 |

\* cited by examiner

*Primary Examiner*—Shelley A. Dodson (57) ABSTRACT

A lotion includes a micro-emulsion composition, which is liquid at room temperature and undergoes a phase change to a semi-solid or solid upon contact with a substrate. The micro-emulsion composition can include a polar emollient, a non-polar emollient, a non-ionic surfactant, and a co-surfactant. The invention also includes a substrate treated with the lotion.

50 Claims, 7 Drawing Sheets

WATERLESS LOTION AND LOTION-TREATED SUBSTRATE

BACKGROUND OF THE INVENTION

1. Field of the Invention

The present invention relates to a waterless lotion and substrate treated with the waterless lotion. In particular, the present invention relates to a waterless micro-emulsion lotion which is liquid at room temperature and semi-solid upon contact with a substrate.

2. Description of the Related Art

Numerous examples of lotion formulae for bathroom tissue, facial tissue and non-woven material can be found in the art.

U.S. Pat. No. 5,607,760 to Roe relates to a lotion coating on the outer surface of the non-woven top sheet of an absorbent article, such as diapers, pull-on products, adult incontinence devices, and the like. The lotion composition is reported to convey a desirable therapeutic or protective coating benefit and to be effective in reducing the adherence of bowel movement to the skin. This waterless lotion is solid or semi-solid at 20° C. and the most preferred melting point is 45° C. By being semi-solid or solid at ambient temperature, the lotion does not have a tendency to flow and migrate into the interior of the substrate. According to a process for the application of the lotion to a substrate, the lotion composition is placed in a heated tank operating at a temperature of 63° C., then sprayed onto the substrate by a spray head operating at a temperature of 71° C.

U.S. Pat. No. 5,665,426 to Krzysik et al., discloses a lotion formula that can be applied to a tissue which will remain readily available for transfer to the user's skin to reduce skin irritation and redness. The lotion composition includes from about 30 to about 90 weight percent of oil, from about 10 to about 40 weight percent wax, and from about 5 to about 40 weight percent fatty alcohol. The melting point of the lotion composition is from about 30° C. to about 70° C. The lotion was applied to the tissue via a heated rotogravure printing process. Specifically, the formulation was pre-melted at about 56° C. and the press supply system (supply hose, doctor application head, and gravure roll) was pre-heated at about 50° C. The deposit solidified almost instantaneously on the surface of the treated tissue, dramatically increasing the product's hydrophobicity, and helping prevent "wet-through" to the user's hand.

There is a need in the art to eliminate handling/application issues associated with "hot" lotion and improve the product softness and absorbency of the lotion-treated substrate. In addition to providing these advantages over "hot" lotion, uniformly, the present invention provides an easily applied, stable, substantially liquid lotion which when applied to a cellulosic substrate results in a lotioned product having a lubricious, soothing, non-greasy feeling, gentle and effective, moisturizing benefit for the user's skin.

SUMMARY OF THE INVENTION

One aspect of the present invention includes a lotion including a micro-emulsion composition, which is substantially liquid at room temperature and undergoes a phase change to a semi-solid or solid upon contact with a cellulosic substrate. The micro-emulsion composition includes a polar emollient, a non-polar emollient, a co-surfactant and a non-ionic surfactant.

Another aspect of the present invention includes a substrate treated with the lotion including a micro-emulsion composition, which composition is liquid at room temperature and undergoes a phase change to a semi-solid or solid upon contact with the cellulosic substrate.

Another aspect of the present invention includes a lotion including a micro-emulsion, which includes a polar emollient, a non-polar emollient, a non-ionic surfactant, and a co-surfactant wherein at least one of the emollients has substantial solubility in either cellulosic or synthetic fiber. Preferably, at least the polar emollient is soluble in cellulosic fibers and the non-polar emollient is more preferably soluble in synthetic fibers.

Another aspect of the present invention includes a lotion including: 35% polyalkoxy or polyhydroxy emollient; 12.5% aromatic ester, such as $C_{12}$ to $C_{15}$ alkyl benzoate ester or mineral oil; 12.5% myristyl alcohol; and 40% PEG-20 methyl glucose sesquistearate.

Additional features and advantages of the present invention will be set forth in the detailed description which follows, and in part will be readily apparent to those skilled in the art from that description or recognized by practicing the invention as described herein, including the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DETAILED DESCRIPTION OF PREFERRED EMBODIMENT

The invention relates to a substrate treated with a waterless micro-emulsion lotion, which is liquid at room temperature. For the purposes of the present invention, room temperature is a temperature of from about 20° C. to about 25° C. The lotion formula of the present invention undergoes an in-situ phase change from liquid to semi-solid, finely divided, uniformly dispersed form upon contact with the substrate, for example, the fibers of the web. This property is important in preventing liquid lotion migration into the substrate or the packaging, and in enhancing the lubricious, soft, and non-greasy feeling of the lotioned substrate. Lotion in the substrate is readily transferred to the user's skin by the friction from wiping and body heat to provide the benefits to the skin surface.

Furthermore, this lotion formula is also termed "cold" lotion since it is a liquid at room temperature. The term "hot" or "cold" lotion refers to either the lotion form being solid ("hot") or liquid ("cold") at room temperature and lotion application temperature either higher ("hot") or at room temperature ("cold"). Application of a cold lotion does not require cumbersome and expensive heated delivery equipment. Rather, the lotion can be applied easily by any available technology such as spraying, printing, coating, extrusion or other techniques. The micro-emulsion or "cold" lotion contains an external continuous non-polar or polar emollient, an internal discontinuous polar or non-polar emollient, a surfactant and a mixture of fatty alcohol co-surfactants. The lotion may also contain optional ingredients, including plant extracts, perfume and a medicinal agent.

The lotion of the present invention alleviates handling/application issues associated with a "hot" lotion and improves the product softness and absorbency of the lotion treated substrate. This is achieved by the present waterless, hydrophilic, "cold" lotion, which is liquid at room temperature, that can be applied to the substrate without heating equipment. The lotion is capable of an in-situ phase change from liquid to a semi-solid form upon contact with the web fibers which when loaded prevents lotion free flow and migration. In addition to these advantages over a "hot" lotion, the lotioned product of the present invention also provides a lubricious, soothing non-greasy feeling, gentle and effective cleansing, skin healing and moisturizing benefit for the user's skin. Further, the lotion composition is able to incorporate typical cosmetic additives, preservatives and anti-bacterial agents regardless of the water solubility of the additive. Finally, facial tissue products made from "hot" lotion are usually not recommended for cleaning transparent materials, such as eyeglasses, due to the "hot" lotion leaving a translucent or opaque smear. The present "cold" lotion treated substrates do not suffer this deficiency.

The present invention relates to a substrate treated with a waterless, micro-emulsion lotion, which is liquid at room temperature. The composition preferably includes four basic components: a polar emollient, non-polar emollient, co-surfactant, and non-ionic surfactant.

Preferred polar emollients include a polyhydroxy emollient. Preferred polyhydroxy emollients include propylene glycol, glycol, glycerol, sorbitol, diethylene glycol, methylene glycol, poly propylene glycol, poly ethylene glycol, and the like.

Preferred non-polar emollients include an aromatic or linear ester, Guerbet ester, mineral oil, squalane, squalene, liquid paraffin and the like.

The polar or non-polar emollient is either in the continuous outer phase or in the discontinuous internal phase of the micro-emulsion.

Preferred co-surfactants include fatty alcohols. Preferred fatty alcohols include $C_{12}$ to $C_{18}$ fatty alcohols, behenyl alcohol, iso cetyl alcohol, and iso stearyl alcohol.

Preferred non-ionic surfactants include PEG-20 methyl glucose sesquistearate, PPG-20 methyl glucose ether, PPG-20 methyl glucose ether distearate, PEG-20 methyl glucose distearate, PEG-120 methyl glucose dioleate, ethoxylated methyl glucose having from about 10 to about 20 repeating ethoxy units, and the like.

The compositions of the present invention are chosen to lie within the micro-emulsion region of a given formulation. All percentages, ratios, and proportions of the ingredients within the compositions of the present invention are determined by the micro-emulsion region of a ternary phase diagram of the polar emollient/non-polar emollient/co-surfactant/non-ionic surfactant formulations (PE/NPE/COS/NIS). Outside of the micro-emulsion region on the low percent side of the polar or non-polar emollients, a semi-solid or solid region is preferably present (see FIGS. 1–6). A micro-emulsion is thermodynamically stable and is essentially transparent in the visible region of the spectrum, which typically indicates that particle size diameter is preferably less than about 0.1 micron, or so. When the particle size diameter is greater than about 3,200 A (about 0.32 micron), the liquid is no longer considered a micro-emulsion but is an emulsion which can often appear turbid and be thermodynamically unstable. The micelle structure of a micro-emulsion is either a "direct" type (head out/tail in) or an "inverse" type (head in/tail out). The liquid micro-emulsion increases the surface area of the lipophilic constituent so it contributes significantly to the utility of the present composition in neat form. Fluidity on the skin surface, small particle size, high surface area and high hydrophilic character, are highly desirable properties for cleansing purposes either when the substrate is used by itself or when lotioned products are rewet with water. Any combination or proportion of these ingredients which produces a micro-emulsion can be used.

An important aspect of this invention is when the liquid lotion contacts the fibers or non-woven substrate, it undergoes an in-situ phase change from liquid to semi-solid or solid form. This change results when the substrate web surface fibers absorb the continuous outer phase of the micro-emulsion. The continuous outer phase of the micro-emulsion may be a non-polar or polar-emollient. If it is a polar material, hydrogen bonding can be created between fibers and emollient. Therefore, the percent of the outer phase of the micro-emulsion within the composition is reduced, resulting in shifting the original lotion composition from point A (liquid) inside the micro-emulsion region, to point B or C (semi-solid) outside of the micro emulsion region (see FIGS. 1 to 6). This unique and special characteristic represents an advantage of the invention, in contrast to the lotion of the prior art, in both process application and product performance.

In the application process, the lotion of the invention uses simple and low cost technology relative to the prior art because it is waterless and substantially liquid at room temperature. In contrast, most of the lotions used for treated tissue or non-woven substrate in the prior art are in semi-solid or solid form at room temperature, which requires heated equipment to deliver lotion to the substrate. Furthermore, any delivery technology available can be easily used for application of the lotion of the present invention without heating equipment, such as an air atomized spray coating, brush coater, curtain coater, and direct or offset gravure coating. Cleaning the production line during or after lotion application process due to build-up and solidification of lotion on the conveyer roll is also a serious issue with "hot" lotions. This issue is minimized with the present invention lotion; and in addition, at the converting line, the liquid lotion may act as a lubricant and impede adhesion of "stickies" (gummy deposits from recycle fiber basesheet) on the embossing rolls to improve the converting process and production rate.

The micro-emulsion is liquid at room temperature, but when in contact with the paper or non-woven substrate, the lotion phase changes to semi-solid form. This unique property provides for the liquid "cold" lotion advantages which are primarily associated with "hot" lotion such as: (1) retaining more lotion on the substrate surface; (2) impeding penetration of the lotion into the web without requiring an immobilizing agent; (3) reducing the amount of lotion applied required to enhance the product performances; and (4) reducing the impact of lotion on the physical properties of the tissue. Additionally, if necessary, a higher level add-on of the present lotion can be applied to the substrate as compared to the "hot" lotion due to the liquid form of the "cold" lotion at room temperature. In this case, the hydrophilic nature of the "cold" lotion product will remain resulting in better cleansing or enhanced skin care benefits, in contrast to the hydrophobic "hot" lotion. These cold lotions do not suffer from the common deviancy of hot lotions wherein it is observed that use of too much "hot" lotion can result in the product becoming stiff.

The ability of the continuous outer phase to include either polar or non-polar components provides advantages to the present invention. Both polar and non-polar emollients contribute to the ability of the present invention to accommodate a wide range of compatibility with various additives such as preservatives, anti-bacterial agents, natural therapeutic oils, soothing agents, whether they are soluble or not in the polar or non-polar emollient. In other words, the formulations of the present invention may be designed to be effective at promoting numerous consumer benefits. For example, in a wiper product containing a high add-on level (100% to 300%) of the present lotion for cleansing oil-based dirt or grease on the skin, the preferred lotion composition includes a polar emollient outer phase/non polar oil internal phase/hydrophilic surfactant with co-surfactant fatty alcohol $C_{14}$ to $C_{18}$. After application of the micro-emulsion to the cellulosic substrate, the weight percent of the outer phase polar emollient is preferably very low relative to the non-polar internal phase emollient as the polar phase is strongly absorbed by the cellulosic fibers. In wiping oily skin surfaces, the product releases the non-polar emollient (as a carrier) and the nonionic surfactant. This combination emulsifies the oil-based dirt or grease on the skin and, by encapsulating it inside the micelle structure after wiping, carries it into the internal phase of the cleaning formulation without leaving a non-polar oil phase on the skin. This formulation is well-suited for cleaning of oils. We prefer that the outer phase be polar because the grease or oil goes into the non-polar phase on the wipe and thus may be removed. This micro-emulsion with a polar outer phase is believed better for cleansing oil from the skin surface than using a lotion formulation of non-polar oil emollient outer phase/polar emollient internal phase/nonionic surfactant plus co-surfactant because lotions having a non-polar continuous phase micelle structure contacts the skin with the oily phase, thus the non-polar outer phase only dissolves the contaminant and, thus, can leave both the oil-based contaminant and non-polar oil phase on the skin surface. Thus a product treated with formulations having continuous non-polar phases are less desirable for removal of oils or greasy material because non-polar liquid is often left on the skin after wiping.

Conventional liquid lotions for a tissue substrate (oil-in-water emulsion) are well known in the art, but generally have at least 70–80% water in the formula. Water in the lotion formula is undesirable for post treatment of the tissue product because: (1) it limits the amount of lotion that can be applied to the substrate due to the lotion having a low percent solid; (2) the large negative impact on the product's physical properties and problems encountered at the treatment line due to water rewetting and weakening of the paper; and (3) the need to install an oven, or other drying device, on the treatment line for removal of the water in the substrate. The present invention formula is waterless but still maintains the ability of incorporating water-soluble additives into the polar phase, plus easily adding oil soluble additives into the non-polar phase of the lotion. This capability is also an advantage of the "cold" lotion compared to "hot" lotion. Incorporating water-based additives in "hot" lotion is very difficult, due to phase separation and loss of uniform distribution of the additive in the lotion, either before or after application onto the product substrate. Water content in "hot" lotion of up to 10 or 15 percent might eliminate the phase separation problem, but controlling and maintaining water content in a lotion formulation at high temperature (about 75° C. to about 90° C.) during process application can be a difficult task. This disadvantage is avoided by the "cold" lotion of the present invention.

The invention relates to a tissue, towel or napkin, optionally wet-strengthened, or wipe or nonwoven material, such as that used for diaper, incontinence and menstrual pad coverstock that is treated with a nongreasy-feeling lotion. The lotion has the effect of making the treated substrate feel nongreasy, reducing chaffing and irritation when the substrate is applied to the skin, and imparting a lubricious feel. Skin care benefits of the lotionized substrate are expressed whether the invention is used dry or prewetted with water.

The lotion can optionally include a therapeutic amount of a medicinal agent. Medicinal agents include medicines, antipathogenic agents, antimicrobial agents, antibacterial agents, antiviral agents, disinfectants, analgesics, other types of medicine having suitable medicinal properties, and the like. For example, an antibacterial agent can be present in an amount of from about 0.01% to about 10%, preferably from about 0.05% to about 5%, of the lotion. Suitable antimicrobial agents include those effective against human pathogens, such as *escherichia coli, staphylococcus aureus, salmonella chloreraesuis, salmonella typhi, pseudomonas aeruginosa, pseudomonas cepacia*, and the *candida* species, including *albicans*. Specific antimicrobial agents suitable for use in the lotion of the invention include 2,4,4'-trichloro-2'-hydroxy-diphenyl ether (triclosan); 3,4,4'-trichlorocarbanilide (triclocarban); 3,4,4'-trifluoromethyl-4,4'-dichlorocarbanilide (cloflucarban); 5-chloro-2-methyl-4-isothiazolin-3-one; iodopropynlbutylcarbamate; 8-hydroxyquinoline; 8-hydroxyquinoline citrate; 8-hydroxyquinoline sulfate; 4-chloro-3,5-xylenol(chloroxylenol); 2-bromo-2-nitropropane-1,3-diol; diazolidinyl urea; butoconazole; nystatin; terconazole; nitrofurantoin; phenazopyridine; acyclovir; clortrimazole; chloroxylenol; chlorhexidine; chlorhexidine gluconate; miconazole; terconazole; butylparaben; ethylparaben; methylparaben; methylchloroisothiazoline; methylisothiazoline; a mixture of 1,3-bis(hydroxymethyl)-5,5-dimethylhydantoin and 3-iodo-2-propynyl butyl carbamate; oxyquinoline; EDTA; tetrasodium EDTA; p-hydroxyl benzoic acid ester; alkyl pyridinum compounds; quaternary ammonium compounds, such as coco phosphatidyl PG-dimonium chloride; mixtures thereof; and the like. Other preferred antimicrobial agents include derivatives of substituted N-alkyl imidazolines disclosed in U.S. Pat. No. 4,078,071 to Walker, issued Mar. 7, 1978, which is incorporated hereby in reference in its entirety.

An anti-viral agent can be present in an amount of from about 0.025% to about 5%, preferably from about 0.05% to about 2.5%, of the lotion. Suitable anti-viral agents include those effective against, or at least retardant toward Corona virus, Picorna virus, Rhino virus, Herpes simplex, Herpes genitalis, Herpes labialis, Respiratory Syncytial Virus (RSV), Para influenza, Cytomegalovirus, Adenovirus, Condyloma and certain synergistic disease states that can involve a virus and a protozoa or a virus and any unfriendly enzymes, e.g., protease, lipase and amylase, that cause a compromised skin as a precursor state for a viral infection to occur. Specific anti-viral agents suitable for use in the lotion of the present invention include bioflavonoids such as hesperitin, naringin, catechin and certain selected amino acids of leguminous origin such as L-canavanine and an analog of L-arginine; dicarboxylic acids such as malonic, glutaric, citric, succinic, and diglycolic acids; alpha hydroxy carboxylic acid such as D-galacturonic acid from Sterculia urens; neem seed oil (*Azadirachta indica*) in its un-denatured form; sandalwood oil (*Santalum album* L.) in its un-denatured form. Optionally, the anti-viral agent could be admixed with at most about 50% by weight of the anti-viral agent of a protease inhibitor such as zinc oxide or other suitable zinc salt.

The lotion can optionally include fragrance. The fragrance can be present in an amount of from 0.01% to about 2%. Suitable fragrance includes volatile aromatic esters, non-aromatic esters, aromatic aldehydes, non-aromatic aldehydes, aromatic alcohols, non-aromatic alcohols, heterocyclic aroma chemicals, and natural floral fragrances, such as blossom, carnation, gardenia, geranium, iris, hawthorne, hyacinth and jasmine.

The lotion can optionally include natural or synthetic powder like talc, mica, boron nitride, silicone, or mixtures thereof.

The substrate web of the present invention optionally includes a wet strength agent. The wet strength agent includes temporary as well as permanent wet strength agents. Suitable wet strength agents include glyoxal; glutaraldehyde; uncharged chemical moieties selected from a group consisting of dialdehydes, aldehyde-containing polyols, uncharged aldehyde-containing polymers, and cyclic ureas and mixtures thereof, and aldehyde-containing cationic starch; mixtures of polyvinyl alcohol and salts of multivalent anions, such as boric acid or zirconium ammonium carbonates; glyoxalated polyacrylamide; polyamide-epichlorohydrin; polyamine-epichlorohydrin; urea-formaldehyde; melamine-formaldehyde; polyethyleneimine; and latex emulsions.

The lotion composition can include other optional components typically present in lotions of this type. These optional components include a botanical extract, such as aloe extract, avocado oil, basil extract, sesame oil, olive oil, jojoba oil, chamomile extract, eucalyptus extract, peppermint extract, as well as animal oils such as emu oil, cod liver oil, orange roughy oil, mink oil, and the like. The lotion of the present invention can also optionally include a humectant. Humectants are hygroscopic materials with a two-fold moisturizing action including water retention and water absorption. Humectants prevent the loss of moisture from skin and help to attract moisture from the environment. Preferred humectants include glycerol, hydrolyzed silk, ammonium lactate, hydroxypropyltrimonium hydrolyzed silk, hydroxypropyl chitosan, hydroxypropyltrimonium hydrolyzed wheat protein, lactamidopropyltrimonium chloride, and ethyl ester of hydrolyzed silk. The botanical extract, animal oil or humectant is preferably present in an amount of less than about 3% when used in the base formulation of the lotion. Further optional components include a skin refreshing agent such as encapsulated water in oil, eucalyptus oil, and menthol oil. All of these optional materials are well known in the art as additives for such formulations and can be employed in appropriate amounts in the lotion compositions of the present invention by those skilled in the art.

The substrate of the present invention can be any suitable applicator that the lotion can be retained upon. Suitable substrates include a web, gauze, cotton swab, transdermal patch, container or holder. The lotion may be retained on the substrate in any convenient amount.

The web of the present invention can be any suitable substrate web, including a flushable or nonflushable web of cellulosic fibers; a web of synthetic fibrous material; tissue, towel or napkin, optionally wet-strengthened; wipe or nonwoven material, such as that used for diaper, incontinence and menstrual pad cover-stock; and the like. Suitable synthetic fibrous material includes meltblown polyethylene, polypropylene, copolymers of polyethylene and polypropylene, bicomponent fibers including polyethylene or polypropylene, and the like. The substrate also may be embossed.

The present invention includes a flushable or nonflushable web of cellulosic fibers treated on at least one side thereof, preferably in an amount of from about 0.1% to about 25%, more preferably from about 0.5% to about 20%, by weight of the dried fiber web with the lotion of the present invention. The present invention further relates to a web of synthetic fibrous material treated on at least one side thereof, preferably in an amount of from about 0.1% to about 25%, more preferably from about 0.5% to about 20%, by weight of the dried web with the lotion of the present invention.

The substrate can be prepared according to conventional processes (including TAD, CWP and variants thereof) known to those skilled in the art. The substrate may be creped or uncreped. Lotion can be applied to the substrate according to conventional application methods known to those skilled in the art.

EXAMPLES

Formulations of the substantially waterless micro-emulsion of this invention were prepared in which, the components, their ratios and the conditions selected to provide micro-emulsion subject to in-situ phase change upon contact with a cellulosic substrate were varied as shown in the following Examples.

In preparing each formulation the following general procedure was used. The polar phase propylene glycol was mixed with surfactant and co-surfactant in a heated container at about 60° C. to about 70° C. until the chemicals are completely melted. The non-polar oil phase is added to the mixture with moderate agitation for about 10 minutes, then cooled to room temperature. At this point the lotion is in clear liquid form and ready to apply to the substrate. The micro-emulsion forms spontaneously without the need for a high shear mechanical device and is stable indefinitely.

Examples 1–7

Examples 1 to 7 were prepared in accordance with the present invention. These lotion formulas are liquid at room temperature, transparent, very stable and accordingly the lotion ingredient ratios are inside the micro-emulsion region of the phase diagrams from FIG. 1 (Example 1), FIG. 2 (Example 2), FIG. 3 (Example 3), FIG. 4 (Example 4), FIG. 5 (Examples 5 and 6). Surprisingly, the lotion of the present invention is characterized as having a good hand-feel perception and non-greasy hand-feel, which is thought to be due to the particle size of the micro-emulsion being too small to be detected in the oil phase by the fingertips.

TABLE 1

| Ingredients | Ex. 1 (%) | Ex. 2 (%) | Ex. 3 (%) | Ex. 4 (%) | Ex. 5 (%) | Ex. 6 (%) | Ex. 7 (%) |
| --- | --- | --- | --- | --- | --- | --- | --- |
| Propylene glycol | 35 | 35 | 5 | 15 | 15 | 30 | 35 |
| Finsolv TN[(1)] | 12.5 | 0 | 16 | 0 | 30 | 15 | 0 |
| Carnation Oil[(2)] | 0 | 0 | 0 | 0 | 0 | 0 | 12.5 |
| Isopropyl myristate | 0 | 15 | 0 | 30 | 0 | 0 | 0 |
| Lambert CE 2000[(3)] | 0 | 0 | 4 | 0 | 0 | 0 | 0 |
| Myristyl alcohol ($C_{14}$) | 12.5 | 15 | 0 | 0 | 0 | 0 | 12.5 |
| Kalcol 1618[(4)] | 0 | 0 | 7.5 | 0 | 5.5 | 5.5 | 0 |
| Glucam P-20 Distearate[(5)] | 0 | 0 | 67.5 | 0 | 49.5 | 49.5 | 0 |
| Glucamate SSE-20[(6)] | 40 | 35 | 0 | 55 | 0 | 0 | 40 |

[(1)]Finsolv TN: $C_{12}$ to $C_{15}$ alkyl benzoate ester from Finetex Inc.
[(2)]Carnation: Mineral oil from Witco Corp.
[(3)]Lambert CE 2000: tri-octyldodecyl-citrate (Guerbet ester) from Lambert Technologies.
[(4)]Kalcol 1618: Mixture 50/50 of cetyl alcohol ($C_{16}$) and stearyl alcohol ($C_{18}$) from Kao Corp.
[(5)]Glucam P-20 Distearate: PEG-20 methyl glucose distearate from Amerchol.
[(6)]Glucamate SSE-20: PEG-20 methyl glucose sesquistearate from Amerchol.

Example 8

Figure 1:
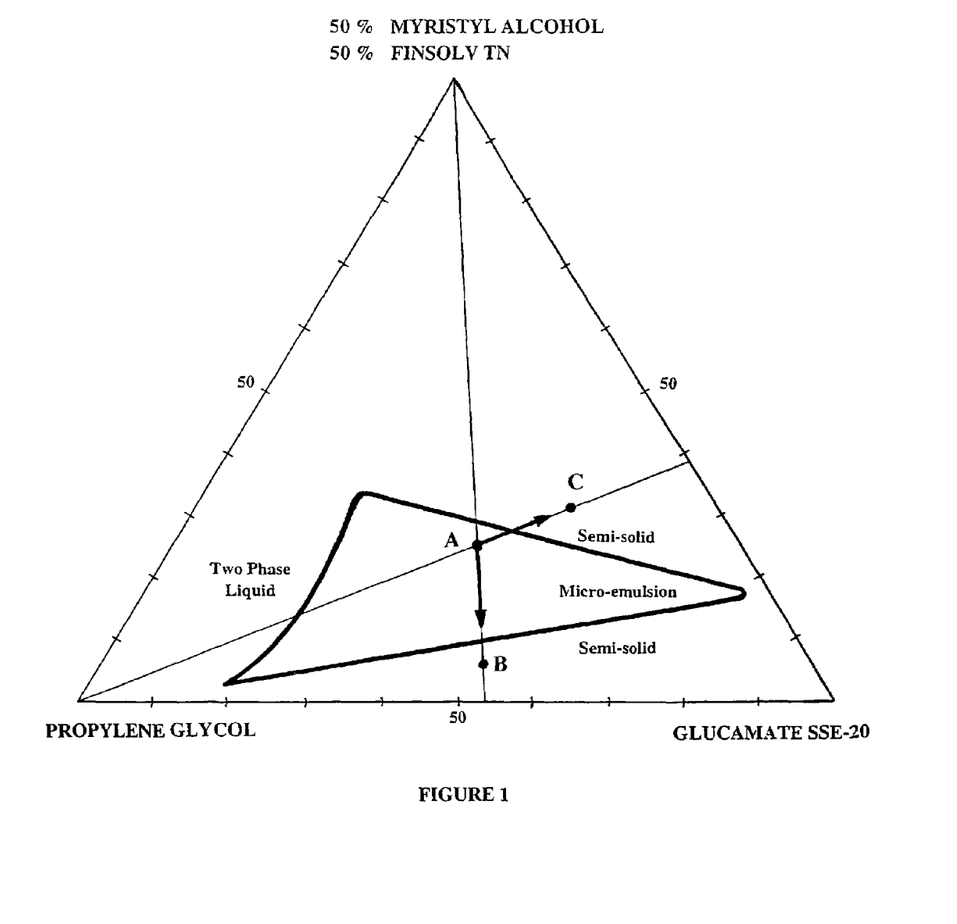
FIG. 1 is a partial phase diagram of an embodiment of the present invention at room temperature showing the micro-emulsion region of the phase diagram.
Figure 2:
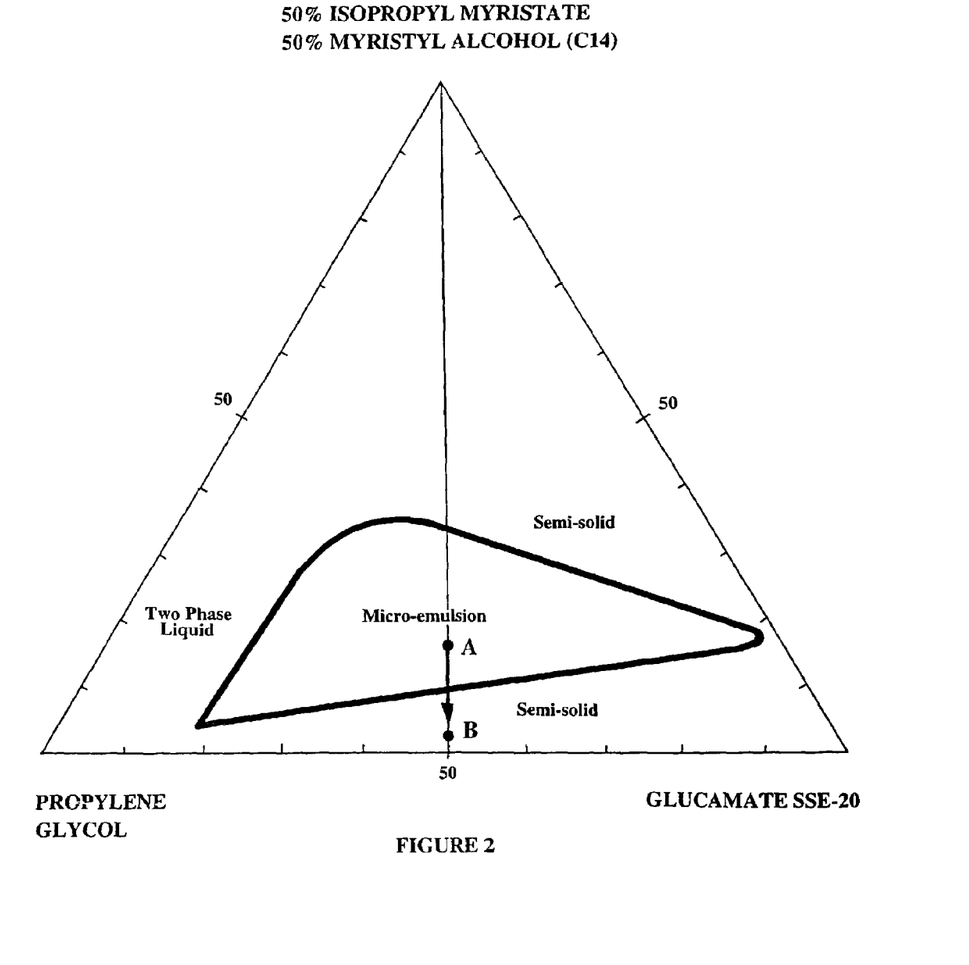
FIG. 2 is a partial phase diagram of another embodiment of the present invention at room temperature showing the micro-emulsion region of the phase diagram.
Figure 3:
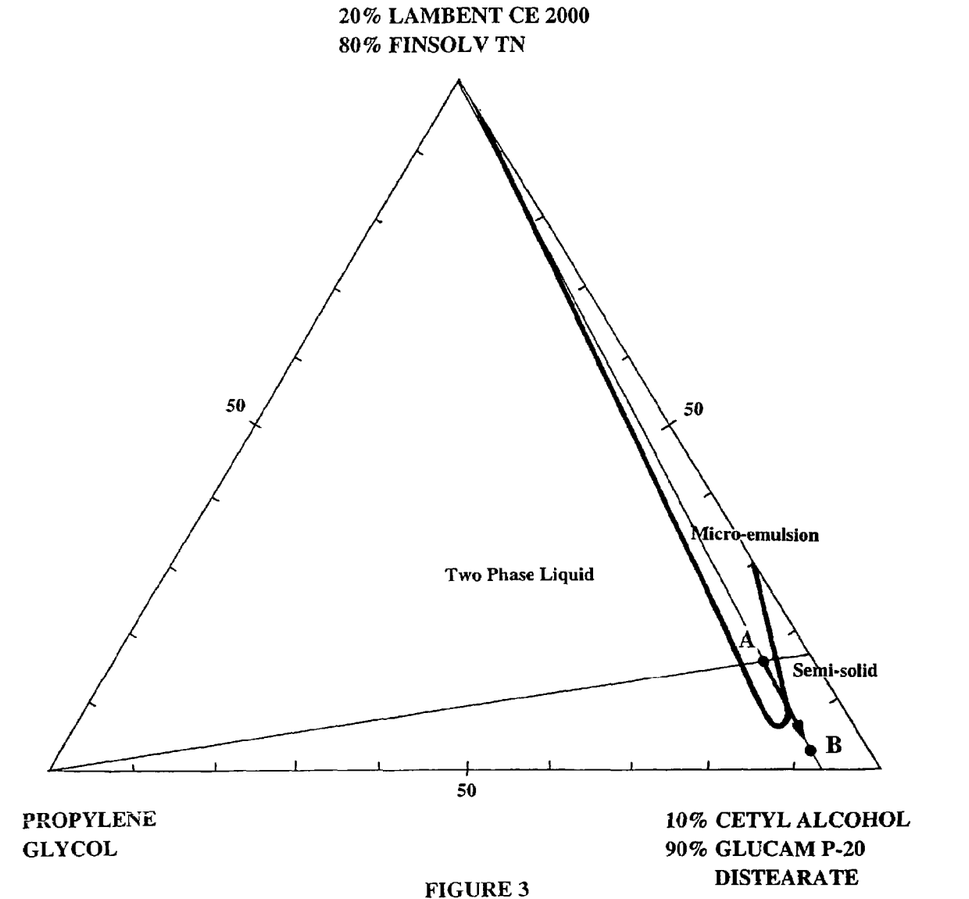
FIG. 3 is a partial phase diagram of another embodiment of the present invention at room temperature showing the micro-emulsion region of the phase diagram.
Figure 4:
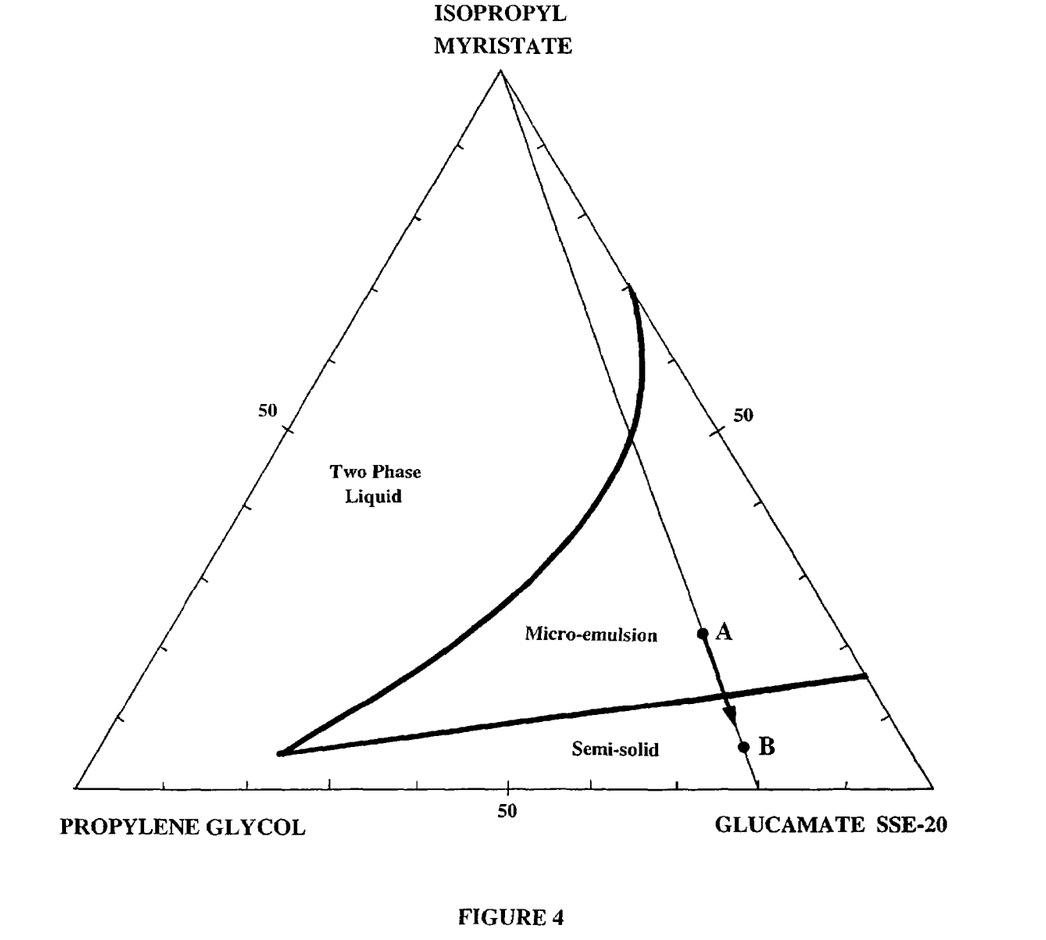
FIG. 4 is a partial phase diagram of another embodiment of the present invention at room temperature showing the micro-emulsion region of the phase diagram.
Figure 5:
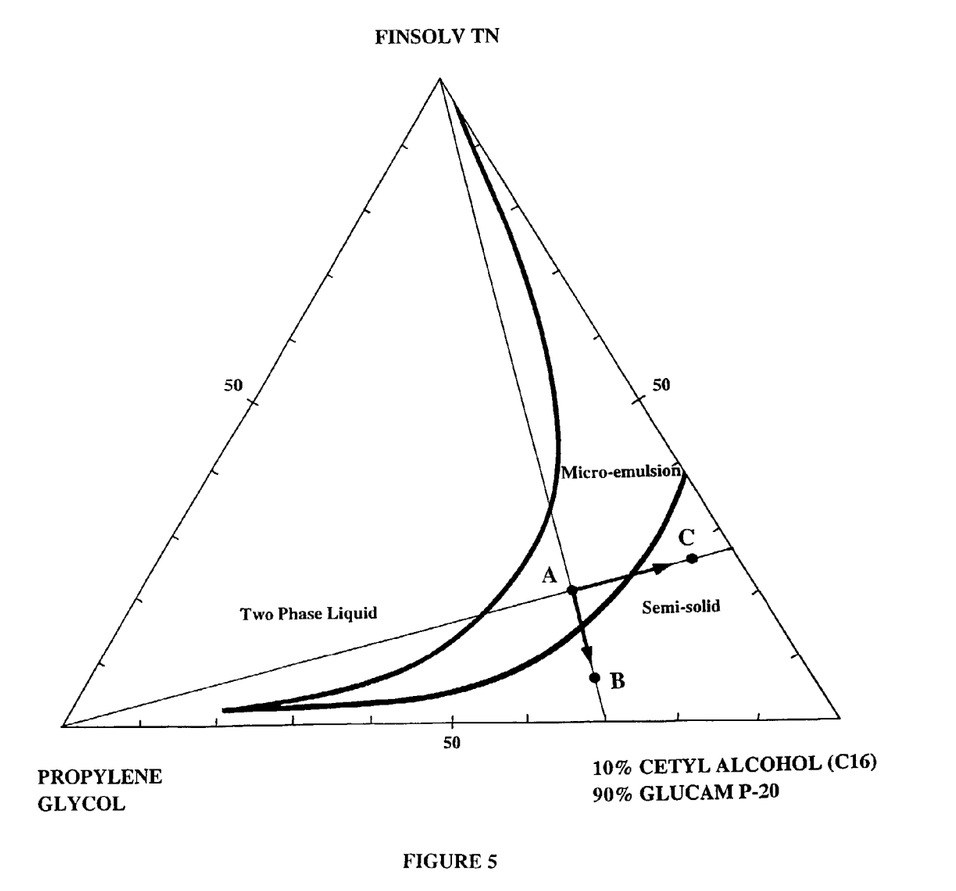
FIG. 5 is a partial phase diagram of another embodiment of the present invention at room temperature showing the micro-emulsion region of the phase diagram.
Figure 6:
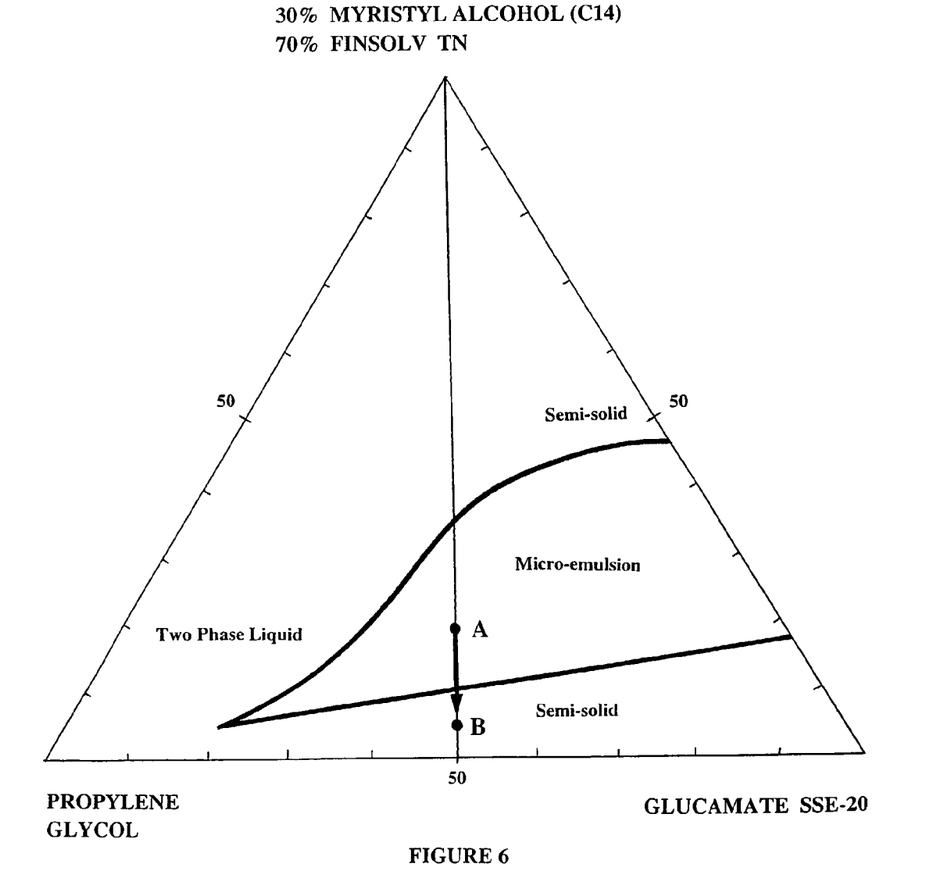
FIG. 6 is a partial phase diagram of another embodiment of the present invention at room temperature showing the micro-emulsion region of the phase diagram.
Figure 7:
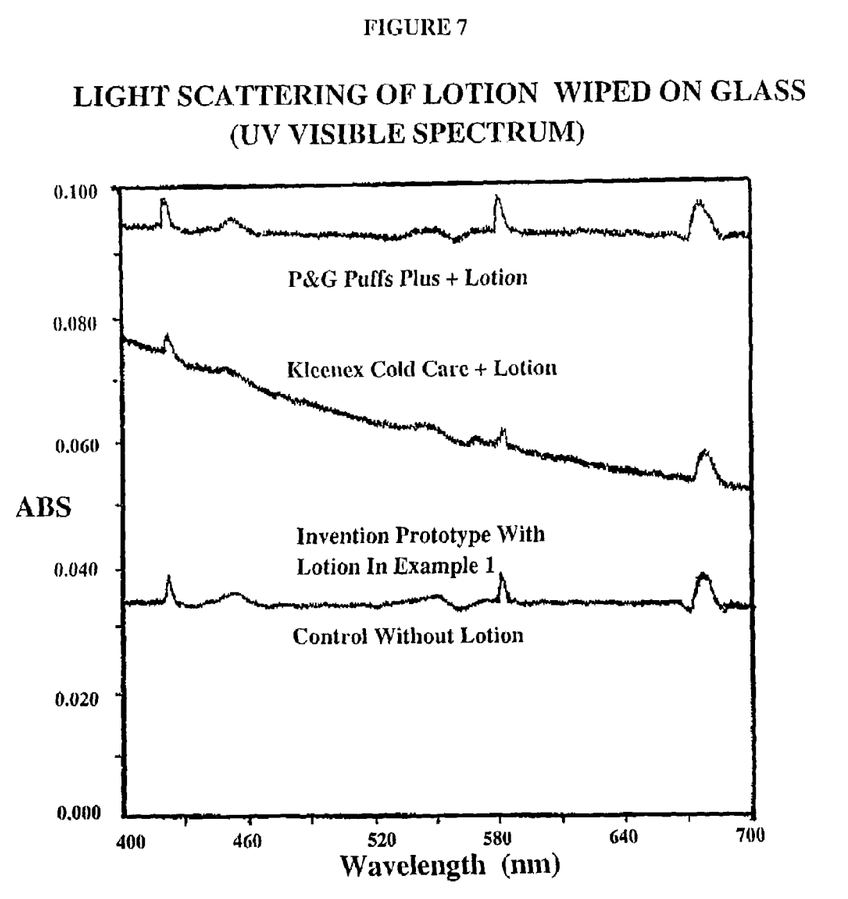
FIG. 7 is a spectrum of the lotion residue transferred to a glass microscope slide after wiping with several lotioned substrates.

The lotion prepared in Example 1 was applied to a tissue basesheet at a 5% add-on level, then converted to a two ply tissue product. The product was tested for the amount of lotion transferred to the skin. The results were compared with commercially available lotioned tissues by comparing the light reflection of cold lotion residual on glass relative to that from two other products. The scattering of light caused by lotion smeared onto the glass microscope slide is measured by using the UV/visible spectrophotometer in the wavelength region from 700 nm to 400 nm. Lotion was transferred to the slide by holding it between two layers of lotioned tissue for 30 seconds and then rubbing the tissue over the slide 20 times in 15 seconds. The lotion smeared glass slide was placed in the sample beam of a double beam UV/Visible spectrometer to measure the light scattering. The results in FIG. 7 show that scattering of light caused by lotion smeared onto the slide rubbed with the tissue treated with the lotion in Example 1, looked identical to the control (untreated tissue). However, the two commercially available lotioned facial tissue products tested produced a significant amount of light scattering compared to the lotioned tissue of the present invention. In fact, the containers for these commercial products specifically state "not recommended for cleaning eyeglasses." In addition, from the lab test result, the amount of lotion transferred by the lotioned substrate of the present invention to the skin is measured to be about 4.2 mg/$cm^2$.

The lotioned substrate product of the present invention is able to transfer lotion to the skin for enhancing skin care benefits, while also being able to "wipe eyeglasses and still maintain clear vision." These properties of the present invention represent significant advantages over the lotioned facial tissues of the prior art.

Examples 9 and 10

The lotion treated substrate web of the present invention optionally includes a wet strength agent. The wet strength agent includes permanent as well as temporary wet strength. Example 10 illustrates cross directional wet tensile decay versus soaking time of the present invention basesheet treated with temporary wet strength agent glyoxalated poly (acryamide-co-DADMAC) with 5% of the lotion of Example 1. The cross directional wet tensile (CD wet tensile) is measured by the Finch Cup Test method.

TABLE 2

| Times (minutes) | Example 9 Control (without lotion) | | Example 10 Treated Product (with lotion) | |
| --- | --- | --- | --- | --- |
| | CD Wet Tensile (G/3") | (%) Wet CD Lost (%) | CD Wet Tensile (G/3") | (%) Wet CD Lost (%) |
| 0 | 47 | — | 40.5 | — |
| 1 | 40 | 15% | 35 | 14% |
| 2 | 36 | 23% | 32 | 21% |
| 4 | 32 | 32% | 25 | 38% |
| 8 | 30 | 36% | 25 | 38% |

The data in Table 2 indicates that after 4 minutes of soaking in tap water, the percent CD wet tensile lost of the present invention (Example 10) is greater than the control without lotion (Example 9). This is a surprising property of the present invention because a tissue product treated with the hot lotion of the prior art usually tends to reduce the product's hydrophilic properties, therefore, the break up times or the sinking times in tap water is usually increased. This feature of the present invention is important for preventing the clogging of toilets and septic systems, while maintaining a desirable initial wet strength level during use.

We claim:

1. A lotion comprising a micro-emulsion composition, which is liquid at room temperature and undergoes a phase change to a semi-solid or solid upon contact with a substrate.

2. The lotion of claim 1, wherein said substrate is a non-woven web and said lotion undergoes the phase change upon contact with the fibers of the web.

3. The lotion of claim 1, wherein said lotion comprises a continuous outer phase and a discontinuous internal phase.

4. The lotion of claim 3, wherein said contact with said substrate results in the substrate absorbing a portion of the continuous outer phase such that the percent of the outer phase in the micro-emulsion composition is decreased resulting in the phase change to a solid or semi-solid.

5. The lotion of claim 1, further comprising an additive.

6. The lotion of claim 5, wherein said additive comprises a preservative, anti-bacterial agent, natural therapeutic oil, soothing agent, or combination thereof.

7. A substrate treated with a lotion comprising a micro-emulsion composition, which composition is liquid at room temperature and undergoes a phase change to a semi-solid or solid upon contact with the substrate.

8. The substrate of claim 7, wherein said substrate is a non-woven web and said lotion undergoes the phase change upon contact with the fibers of the web.

9. The substrate of claim 7, wherein said lotion comprises a continuous outer phase and a discontinuous internal phase.

10. The substrate of claim 9, wherein said contact with said substrate results in the substrate absorbing a portion of the continuous outer phase such that the percent of the outer phase in the micro-emulsion composition is decreased resulting in the phase change to a solid or semi-solid.

11. The substrate of claim 7, wherein said lotion further comprises an additive.

12. The substrate of claim 11, wherein said additive comprises a preservative, anti-bacterial agent, natural therapeutic oil, soothing agent, or combination thereof.

13. A lotion comprising a micro-emulsion, which comprises a polar emollient, a non-polar emollient, a non-ionic surfactant, and a co-surfactant.

14. The lotion of claim 13, wherein said polar emollient comprises a polyhydroxy emollient.

15. The lotion of claim 14, wherein said polyhydroxy emollient comprises propylene glycol, glycol, glycerol, or combinations thereof.

16. The lotion of claim 13, wherein said non-polar emollient comprises an aromatic or linear ester, Guerbet ester, mineral oil, or combination thereof.

17. The lotion of claim 13, wherein said co-surfactant comprises a fatty alcohol.

18. The lotion of claim 17, wherein said fatty alcohol comprises a $C_{12}$ to $C_{18}$ fatty alcohol or combination thereof.

19. The lotion of claim 13, wherein said non-ionic surfactant comprises PEG-20 methyl glucose sesquistearate, PPG-20 methyl glucose ether distearate, or combinations thereof.

20. The lotion of claim 13, wherein said lotion comprises a continuous outer phase and a discontinuous internal phase.

21. The lotion of claim 13, further comprising an additive.

22. The lotion of claim 21, wherein said additive comprises a preservative, anti-bacterial agent, natural therapeutic oil, soothing agent, or combination thereof.

23. The lotion of claim 13, wherein said lotion is liquid at room temperature and undergoes a phase change to a semi-solid or solid upon contact with a substrate.

24. The lotion of claim 23, wherein said substrate is a non-woven web and said lotion undergoes the phase change upon contact with the fibers of the web.

25. A substrate treated with a lotion comprising a micro-emulsion, which comprises a polar emollient, a non-polar emollient, a non-ionic surfactant, and a co-surfactant.

26. The substrate of claim 25, wherein said polar emollient comprises a polyhydroxy emollient.

27. The substrate of claim 26, wherein said polyhydroxy emollient comprises propylene glycol, glycol, glycerol, or combinations thereof.

28. The substrate of claim 25, wherein said non-polar emollient comprises an aromatic or linear ester, Guerbet ester, mineral oil, or combination thereof.

29. The substrate of claim 25, wherein said co-surfactant comprises a fatty alcohol.

30. The substrate of claim 29, wherein said fatty alcohol comprises a $C_{12}$ to $C_{18}$ fatty alcohol or combination thereof.

31. The substrate of claim 25, wherein said non-ionic surfactant comprises PEG-20 methyl glucose sesquistearate, PPG-20 methyl glucose ether distearate, or combinations thereof.

32. The substrate of claim 25, wherein said lotion comprises a continuous outer phase and a discontinuous internal phase.

33. The substrate of claim 25, wherein said lotion further comprises an additive.

34. The substrate of claim 33, wherein said lotion additive comprises a preservative, anti-bacterial agent, natural therapeutic oil, soothing agent, or combination thereof.

35. The substrate of claim 25, wherein said lotion is liquid at room temperature and undergoes a phase change to a semi-solid or solid upon contact with the substrate.

36. The substrate of claim 25, wherein said substrate is a non-woven web and said lotion undergoes the phase change upon contact with the fibers of the web.

37. A lotion comprising: propylene glycol; $C_{12}$ to $C_{15}$ alkyl benzoate ester; myristyl alcohol; and PEG-20 methyl glucose sesquistearate combined in proportions which result in a stable micro-emulsion.

38. A lotion comprising: propylene glycol; isopropyl myristate; myristyl alcohol; and PEG-20 methyl glucose sesquistearate combined in proportions which result in a stable micro-emulsion.

39. A lotion comprising: propylene glycol; $C_{12}$ to $C_{15}$ alkyl benzoate ester; tri-octyldodecyl-citrate; a 50/50 mixture of cetyl alcohol and stearyl alcohol; and PEG-20 methyl glucose distearate combined in proportions which result in a stable micro-emulsion.

40. A lotion comprising: propylene glycol; isopropyl myristate; and PEG-20 methyl glucose sesquistearate combined in proportions which result in a stable micro-emulsion.

41. A lotion comprising: propylene glycol; $C_{12}$ to $C_{15}$ alkyl benzoate ester; a 50/50 mixture of cetyl alcohol and stearyl alcohol; and PEG-20 methyl glucose distearate combined in proportions which result in a stable micro-emulsion.

42. A lotion comprising: propylene glycol; $C_{12}$ to $C_{15}$ alkyl benzoate ester; a 50/50 mixture of cetyl alcohol and stearyl alcohol; and PEG-20 methyl glucose distearate combined in proportions which result in a stable micro-emulsion.

43. A lotion comprising: propylene glycol; mineral oil; myristyl alcohol; and PEG-20 methyl glucose sesquistearate combined in proportions which result in a stable micro-emulsion.

44. A substrate treated with the lotion of claim 37.

45. A substrate treated with the lotion of claim 38.

46. A substrate treated with the lotion of claim 39.

47. A substrate treated with the lotion of claim 40.

48. A substrate treated with the lotion of claim 41.

49. A substrate treated with the lotion of claim 42.

50. A substrate treated with the lotion of claim 43.

* * * * *